US011324409B2

(12) United States Patent
Bahmanyar et al.

(10) Patent No.: US 11,324,409 B2
(45) Date of Patent: May 10, 2022

(54) IMPLANTABLE DEVICE FOR SENSING INTRAVASCULAR PRESSURE

(71) Applicant: IP2IPO INNOVATIONS LIMITED, London (GB)

(72) Inventors: Mohammad Reza Bahmanyar, London (GB); Christopher Neil McLeod, London (GB)

(73) Assignee: IP2IPO INNOVATIONS LIMITED, London (GB)

( * ) Notice: Subject to any disclaimer, the term of this patent is extended or adjusted under 35 U.S.C. 154(b) by 379 days.

(21) Appl. No.: 16/346,804

(22) PCT Filed: Nov. 2, 2017

(86) PCT No.: PCT/GB2017/053313
§ 371 (c)(1),
(2) Date: May 1, 2019

(87) PCT Pub. No.: WO2018/083486
PCT Pub. Date: May 11, 2018

(65) Prior Publication Data
US 2019/0246912 A1 Aug. 15, 2019

(30) Foreign Application Priority Data
Nov. 2, 2016 (GB) ..................... 1618508

(51) Int. Cl.
*A61B 5/0215* (2006.01)
*A61B 5/00* (2006.01)

(52) U.S. Cl.
CPC .......... *A61B 5/0215* (2013.01); *A61B 5/0031* (2013.01); *A61B 2562/0204* (2013.01)

(58) Field of Classification Search
CPC ... A61B 5/0215; A61B 5/0031; A61B 5/6847; A61B 2562/0204; H01L 33/46
See application file for complete search history.

(56) References Cited

U.S. PATENT DOCUMENTS

| 8,764,677 B2 | 7/2014 | Toumazou et al. |
| 2004/0082867 A1 | 4/2004 | Esch et al. |

(Continued)

FOREIGN PATENT DOCUMENTS

| GB | 2558708 A | 7/2018 |
| GB | 2558730 A1 | 7/2018 |
| WO | 2018083486 A1 | 5/2018 |

OTHER PUBLICATIONS

PCT Written Opinion for Appl No. PCT/GB2017/053313 dated Jan. 26, 2018, 5 pages.

(Continued)

*Primary Examiner* — Daniel L Cerioni
*Assistant Examiner* — Raymond P Dulman
(74) *Attorney, Agent, or Firm* — Maine Cernota & Rardin (57) ABSTRACT

An implantable device for sensing intravascular pressure, the device comprising a bulk acoustic wave (BAW) resonator arranged to be deflected by changes in intravascular fluid pressure to provide a pressure dependent sensing signal and an acoustic reflector arranged to separate the BAW resonator from the intravascular fluid and to mediate pressure from the intravascular fluid to the BAW resonator wherein the acoustic reflector comprises a layer structure arranged to provide a series of transitions in acoustic impedance between the intravascular fluid and the BAW resonator.

17 Claims, 6 Drawing Sheets

(Section A-A)

(56) References Cited

U.S. PATENT DOCUMENTS

| | | | |
|---|---|---|---|
| 2005/0068124 A1* | 3/2005 | Stoemmer | H03H 9/585 |
| | | | 333/189 |
| 2010/0056888 A1 | 3/2010 | Skerl et al. | |
| 2013/0176085 A1* | 7/2013 | Barber | H03H 3/04 |
| | | | 333/187 |
| 2013/0181579 A1 | 7/2013 | Shin et al. | |
| 2019/0343388 A1* | 11/2019 | Bahmanyar | B60L 53/80 |

OTHER PUBLICATIONS

PCT Search Report for Appl No. PCT/GB2017/053313 dated Jan. 26, 2018, 3 pages.
Great Britain Search Report for Appl No. GB1718209.8 dated Nov. 6, 2019, 43 pages.
PCT Written Opinion for Appl No. PCT/GB2017/053313 dated Jan. 26, 2018, 12 pages.

* cited by examiner

Figure 1

(Section A-A)

IMPLANTABLE DEVICE FOR SENSING INTRAVASCULAR PRESSURE

RELATED APPLICATIONS

This application is a national phase application filed under 35 USC § 371 of PCT Application No. PCT/GB2017/053313 with an International filing date of Nov. 2, 2017 which claims priority of GB Patent Application 1618508.4 filed Nov. 2, 2016. Each of these applications is herein incorporated by reference in their entirety for all purposes. This application is related to PCT Application No. PCT/GB2017/052801 with an International filing date of Sep. 20, 2017 which claims priority of GB Patent Application 1616096.2 filed Sep. 21, 2016; PCT/GB2017/052802 with an International filing date of Sep. 20, 2017 which claims priority of GB Patent Application 1616090.5 filed Sep. 21, 2016; PCT Application No. PCT/GB2017/052804 with an International filing date of Sep. 20, 2017 which claims priority of GB Patent Application 1616091.3 filed Sep. 21, 2016; and PCT Application No. PCT/GB2017/052834 with an International filing date of Sep. 21, 2017 which claims priority of GB Patent Application 1616092.1 filed Sep. 21, 2016; each of these applications is herein incorporated by reference in their entirety for all purposes.

FIELD

The present invention relates to implantable devices. In particular, the invention relates to implantable devices for sensing intravascular pressure.

BACKGROUND

It is desirable to provide a means for long-term clinical monitoring of patients—for example a patient's intravascular fluid pressure—that avoids the need for repeated use of invasive measurements, which can be uncomfortable for a patient and can affect a patient's health. One way of addressing this concern is by using implantable devices, which can be implanted intravascularly and can function to allow numerous measurements to be taken over a period of time without causing the patient discomfort, and indeed risk to the patient, each time a measurement is required to be taken.

Such an implantable device will however require suitable means by which to monitor intravascular fluid pressure accurately and repeatedly, while keeping the size of the device sufficiently compact to make it suitable for use intravascularly (or, indeed, elsewhere in a human or animal body).

SUMMARY

Aspects and embodiments of the present invention are set out in the appended claims. These and other aspects and embodiments of the invention are also described herein.

Described herein is an implantable device for sensing intravascular pressure, the device comprising a bulk acoustic wave (BAW) resonator arranged to be deflected by changes in intravascular fluid pressure to provide a pressure dependent sensing signal; and an acoustic reflector arranged to separate the BAW resonator from the intravascular fluid and to mediate pressure from the intravascular fluid to the BAW resonator; wherein the acoustic reflector comprises a layer structure arranged to provide a series of transitions in acoustic impedance between the intravascular fluid and the BAW resonator.

A BAW resonator arranged to monitor changes in intravascular fluid pressure may offer advantages in view of its ability to act as a transducer for physical and chemical measurements, to implement complex signal processing functions on a small piezoelectric substrate in a completely passive way, and to communicate with remote electronic systems using electromagnetic waves.

By arranging an acoustic reflector to separate the BAW resonator from the intravascular fluid, mass loading of the resonator by the surrounding intravascular fluid can be avoided. Such an arrangement may therefore enhance the quality and/or accuracy of a sensed signal provided by the BAW resonator and may avoid signal losses that could occur through mass loading of the BAW resonator.

Optionally, the layer structure may be arranged to provide at least three of transitions in acoustic impedance.

Optionally, the layer structure may comprise a flexible layer which encloses a fluid layer between the flexible layer and the BAW resonator. Optionally, the fluid layer has lower acoustic impedance than the surrounding (e.g. intravascular) fluid. Optionally, the fluid has a lower acoustic impedance than the BAW resonator. The fluid layer may comprise a gas layer.

Optionally, the fluid layer is held in a sealed enclosure (or "chamber") provided at least in part by the flexible layer. Optionally, a spacer (for example, a rigid spacer) may be provided that surrounds the fluid layer (for example, it 'encircles' the fluid layer such that the upper surface of the BAW resonator is left exposed). Optionally, the flexible layer is mounted onto the spacer, for example to cover the exposed surface of the BAW resonator, whereby to provide the sealed enclosure. Optionally, the flexible layer is arranged to be spaced from the BAW resonator, for example by way of the spacer extending above the height of the BAW resonator. Optionally, said at least one layer may have a thickness of around 1 micron. Optionally, the flexible layer may comprise a metal foil, for example a gold foil.

Optionally, the BAW resonator may comprise aluminium nitride (AlN), for example the piezoelectric element may comprise aluminium nitride, optionally a thin film aluminium nitride.

Optionally, a body for carrying the BAW resonator may be provided, wherein the BAW resonator is disposed between the acoustic reflector and the body. Optionally, the body may comprise a cavity of fluid at a (known) reference pressure arranged so that the BAW resonator can be deflected into the cavity in response to changes in intravascular pressure. Optionally, the body may be joined to the BAW resonator by a hermetic bond which closes the cavity.

Optionally, sensor circuitry may be disposed in the body and arranged to provide an alternating electrical signal to the BAW resonator. Optionally, the sensor circuitry may be disposed in the cavity.

Optionally, the body may carry an antenna for coupling with an alternating electromagnetic field to provide the alternating electrical signal to the sensor circuitry. Optionally, the body may comprise at least one via arranged to connect the antenna to the sensor circuitry. Optionally, the body may comprise silicon.

Optionally, the device may be sized (or dimensioned) to fit within the artery of an animal or human body, for example the pulmonary artery. The device may be particularly suitable for use with an overweight adult human, for example an adult human male.

Optionally, the device may be arranged to be fixed against the arterial wall, for example it may be mounted to an anchoring apparatus that is arranged to hold the device against the wall of the artery, for example the front wall. Optionally, the anchoring apparatus may comprise nitinol wire and/or a bio-absorbable material, which allows it to be absorbed into the tissue of a body (e.g. an "endothelialised device" when deployed in an artery, for example. Such an anchoring apparatus is described in UK Patent Application No. 1616092.1.

Optionally, an antenna may be in electrical communication with the device, for example it may be attached to the device, for transmission of electrical signals, such as electromagnetic (RF) signals.

As used herein, the term "acoustic reflector" may be interchangeable with the term "acoustic mirror".

BRIEF DESCRIPTION OF THE DRAWINGS

Aspects and embodiments will now be described, by way of example only, with reference to the accompanying drawings, in which.

DETAILED DESCRIPTION

Figure 1:
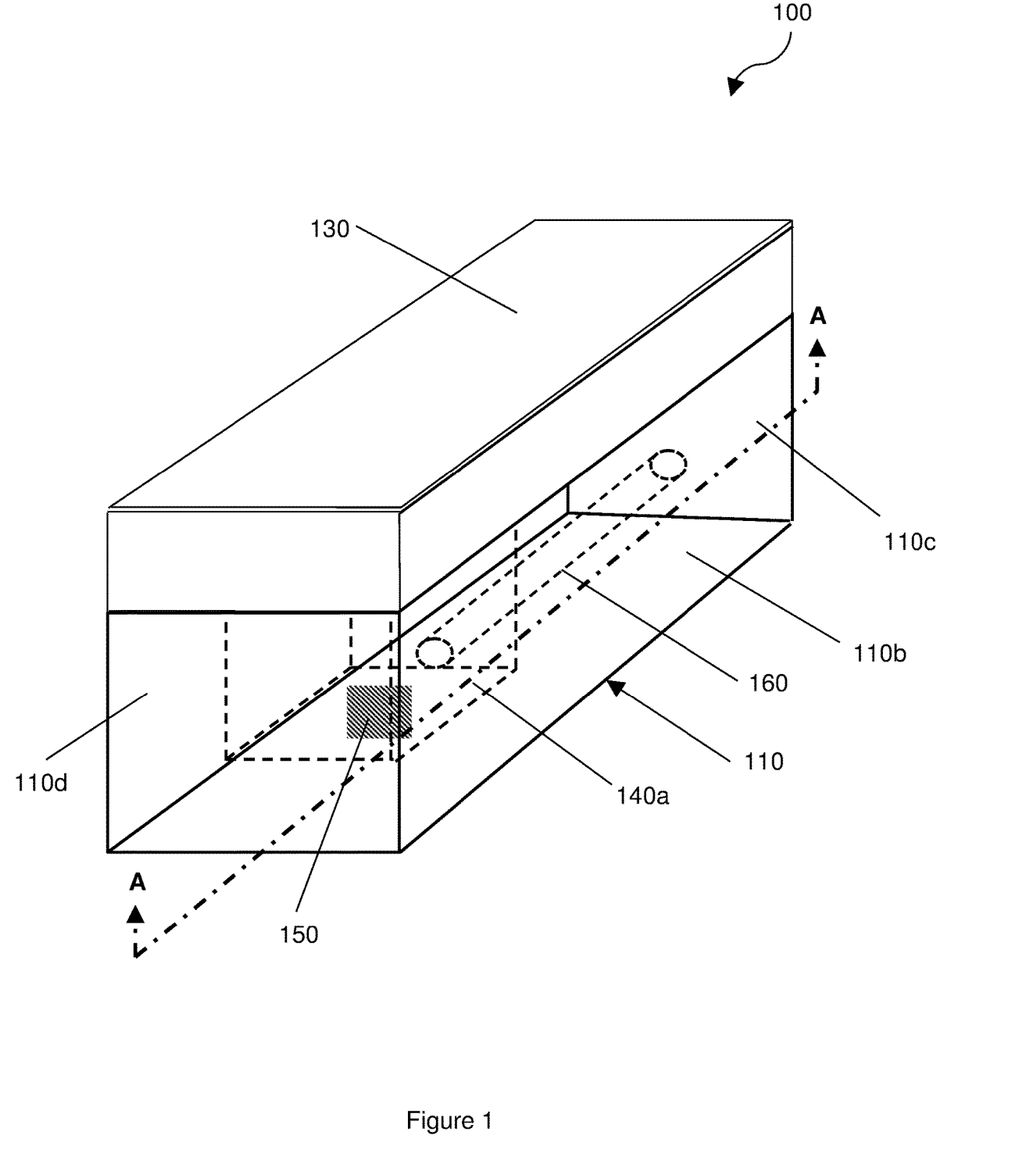
FIG. 1 shows an implantable device.

FIG. 1 shows an implantable device 100 having a body 110 upon which is mounted a bulk wave acoustic (BAW) resonator 120, and an acoustic reflector 130 arranged to cover the BAW resonator 120.

The body 110 is formed as a substantially rectangular cube having an upper surface 110a, a lower surface 110b, a first opposed pair of 'minor' sides 110c and a second opposed pair of 'major' sides 110d, which are at least the same length as the 'minor' sides 110c. The major sides 110d of the body 110 are longer than the minor sides 110c. The height (i.e. the distance between the upper and lower surfaces 110a, 110b) of both the minor and major sides 110c, 110d is the same, such that the upper and lower surfaces 110a, 110b are generally parallel. The height of the body 110 is less than the width of the minor sides 110c of the body 110. The exterior surfaces of the body 110 (i.e. and the sides) are all substantially planar. The body 110 may be made of silicon.

A cavity 140a is provided in the body 110, the cavity 140a extending through the body 110 from the upper surface 110a towards (but not reaching) the bottom surface 110b of the body 110. The cavity 140a is disposed off-centre along the longitudinal axis of the body 110 (i.e. towards a minor side 110c of the body 110). The cavity 140a shown is generally rectangular in cross-section when viewed from the upper surface 110a. The cavity 140a contains a gas (such as air) at a reference pressure, for example atmospheric pressure ($P_{atm}$), and may therefore be referred to as the 'reference' cavity 140a. Sensor circuitry 150 is disposed in the cavity 140a of the body 110, as shown.

A via 160 extends from a minor side 110c of the body 110 into the cavity 140a. The via 160 is arranged to facilitate electrical connection to be made with the sensing circuitry 150 in the cavity 140a. For example, electrical signals may be communicated between the sensing circuitry 150 and an antenna (not shown) carried by the body 110, where the antenna may be arranged to couple with an alternating electromagnetic field, which allows the device 100 to be interrogated on demand, as will be described further on. Such an arrangement may allow the intravascular pressure changes to be obtained from the device 100. Although the via 160 is described as extending from a minor side 110c of the body into the cavity, it will be appreciated in the context of the present disclosure that the via 160 may extend from the bottom surface 110b of the body into the cavity 140a.

The antenna (not shown) may also couple with an alternating electromagnetic field to drive (i.e. provide an alternating electrical signal to) the BAW resonator 120 (via the electrodes 124a, 124b). Thus, a conductive coupling may be provided between the antenna and the electrodes 124a, 124b on the BAW resonator 120 to allow a signal developed by the antenna to be applied to the BAW resonator 120, so as to set up a standing wave in the BAW resonator 120. For example, an electromagnetic (RF) signal may be transmitted to the antenna to excite the BAW resonator 120.

Figure 2:
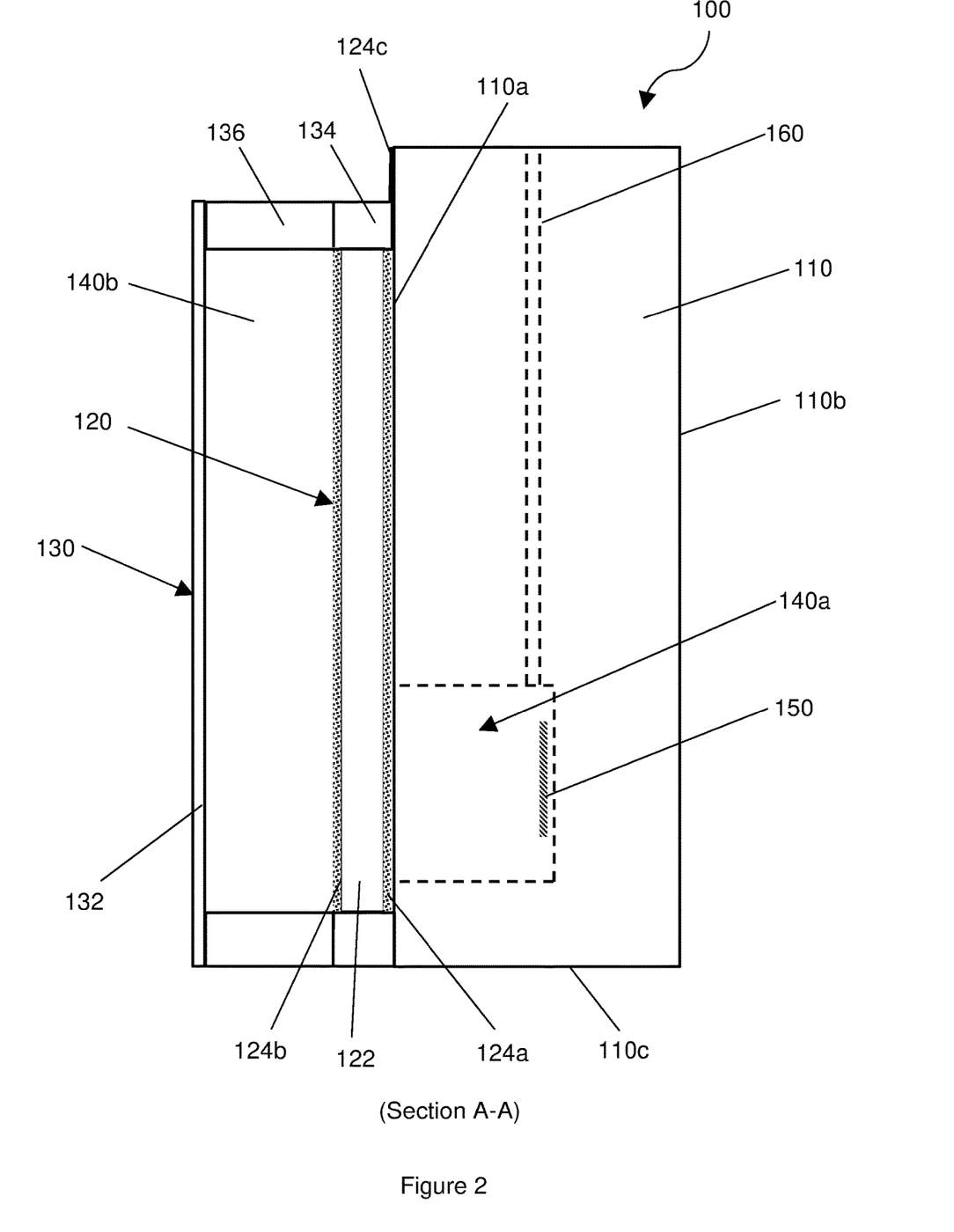
FIG. 2 shows a cut-away view through a side of the implantable device.

The construction of the implantable device 100 is shown in more detail in the sectional view (Section A-A) of FIG. 2. As mentioned above, the device 100 comprises a body 110 having a BAW resonator 120 mounted thereon and an acoustic reflector 130 arranged to cover the BAW resonator 120. The BAW resonator 120 is therefore disposed between the body 110 and the acoustic reflector 130. For example, the BAW resonator may be covered by a flexible membrane which holds a layer of fluid (such as a gas) between the BAW resonator and the membrane. This can create a gas filled chamber which may assist in isolating the BAW resonator 120 from loading by the intravascular fluid.

The BAW resonator 120 is mounted onto the upper surface 110a of the body 110. The BAW resonator 120 is arranged to cover the cavity 140a. The BAW resonator 120 is attached to the body 110 by way of a hermetic bond such that the cavity 140a is hermetically sealed. The BAW resonator 120 comprises a piezoelectric element 122 arranged as a layer sandwiched between two electrodes 124a, 124b. The piezoelectric element 122 may comprise a (piezoelectric) aluminium nitride (AlN) film, for example a 'thin film', which may have a thickness of about 2 microns. The BAW resonator 120 may be arranged to be cantilevered over the cavity 140a. Here, the BAW resonator 120 overlaps the cavity 140a such that it rests on the upper surface 110a of the body 110 adjacent the cavity 140a. As such, the BAW resonator 120 (hermetically) seals the cavity 140a, as mentioned above. The BAW resonator may hermetically seal the cavity 140a. The BAW resonator 120 may overlap the upper surface 110a adjacent the cavity 140a by about 10% of the total distance between the two opposing minor and major sides 110c, 110d, respectively. For example, on a body 110 having a width of 200 microns (e.g. between two minor sides 110c), the BAW resonator 120 may overlap the cavity 140a by about microns. Such an overlap may be acceptable, for example providing structural support, while not significantly damping the BAW resonator 120.

A rigid spacer 134, 136 surrounds (e.g. 'encircles') the BAW resonator 120 leaving its upper surface exposed. The rigid spacer 134, 136 is bonded to the body 110, so as to provide a seal with the body 110. A flexible layer 132a is mounted onto the rigid spacer 134, 136, spaced from the BAW resonator 120 thereby to define a sealed chamber 140b above the BAW resonator 120. The flexible layer 132a may be spaced apart from the BAW resonator 120 by a distance of at least 10 microns, for example.

The chamber 140b contains a fluid chosen to provide lower acoustic impedance than the (e.g. intravascular) fluid that will surround it once implanted into the body. The chamber 140b may therefore be described as providing a fluid layer 132b. In practice, the fluid should be a gas (for example, air), which may be pressurised to about 1 atm.

Thus, the acoustic reflector 130 is provided by a flexible layer 132a and a fluid layer 132b, where the fluid layer 132b is contained within a sealed chamber (e.g. enclosure) provided at least in part by the flexible layer 132a and the BAW resonator 120.

It will be appreciated in the context of the present disclosure that the majority of reflections may occur at the boundary between the BAW resonator 120 and the layer of gas, which is held in place by the membrane of the acoustic reflector.

The flexible layer 132a may comprise a metal foil, for example gold foil, and may have a thickness of at least 1 micron. For example, the flexible layer 132a may have a thickness about 10% of the thickness (e.g. depth) of the fluid layer 140b. The metal foil may be radially corrugated, for example being spiral or circular corrugations, which may help to facilitate large displacements of the flexible layer 132a due to changes in pressure of the surrounding fluid.

Once implanted into a body, the acoustic reflector 130 acts to separate the BAW resonator 120 from surrounding fluid, for example intravascular fluid, while mediating changes in pressure of surrounding fluid to the BAW resonator 120. The acoustic reflector 130 is arranged to provide a series of transitions in acoustic impedance between surrounding fluid and the BAW resonator 120. For example, the acoustic reflector may be arranged to provide at least three transitions in acoustic impedance between the BAW resonator 120, fluid layer 140b and flexible layer 140a. The acoustic reflector 130 may also act to reflect acoustic energy generated by the BAW resonator 120 back to the BAW resonator 120.

The device 100 may be in electrical communication with an antenna (not shown) that is arranged to couple with an alternating electromagnetic (RF) signal. When it is desired to interrogate the implanted device, the antenna may receive an alternating electromagnetic (RF) signal, from external of the human or animal body, which signal is then communicated to the electrodes 124a, 124b of the BAW resonator 120. This signal then generates an acoustic standing wave in the piezoelectric element 122 of the BAW resonator 120. Thus, an alternating electrical signal is applied to the BAW resonator 120 [by the sensing circuitry, which generates a pressure-dependent signal].

A change in pressure of fluid surrounding the device 100 is mediated to the BAW resonator 120 via the acoustic reflector 130. The pressure change causes the BAW resonator 120 to deflect, thereby applying mechanical stress to the piezoelectric element 122. In response to the mechanical stress, the piezoelectric element 122 generates an electrical charge, which alters the characteristics of the acoustic standing wave in the BAW resonator 120

To interrogate the device 100, an alternating electromagnetic RF signal is transmitted to the device via the antenna. Following a change of pressure in the fluid surrounding the device 100, the return signal received from the antenna may have a modified frequency and/or there may be a delay.

The volume of the reference cavity 140a is far greater than the fraction of its volume into which the BAW resonator 120 deflects as a result of an external pressure change. Thus, the membrane 130 separates the BAW resonator 120 from surrounding fluid, while mediating any external pressure changes to the BAW resonator 120 and the pressure change(s) can be determined via deflection of the BAW resonator 120.

One advantage of using a BAW resonator with an implantable device for sensing intravascular pressure may be that the BAW resonator may provide a more robust measurement than, for example, an implantable device that uses a surface acoustic wave (SAW) resonator. Furthermore, by providing an acoustic reflector that separates the BAW resonator from surrounding (e.g. intravascular) fluid, the effect of mass loading on the BAW resonator that may otherwise occur were it to be in direct contact with the surrounding fluid may be mitigated. For example, if such mass loading were to occur it may act to dampen the BAW resonator, which could affect the signal obtained from the BAW resonator (e.g. it could cause significant attenuation of the signal or alter the frequency of a standing wave in the BAW resonator) and hence affect measurements. One advantage of using a BAW resonator with an implantable device for sensing intravascular pressures may be that the BAW resonator may provide a device having smaller profile (e.g. smaller cross section and/or smaller volume) than, for example, an implantable device that uses a surface acoustic wave (SAW) resonator. The acoustic reflector may provide at least partial isolation, e.g. by means of a membrane and a second gas filled chamber, to reduce vibration dissipation from the BAW resonator.

Figures 3A, 3B:
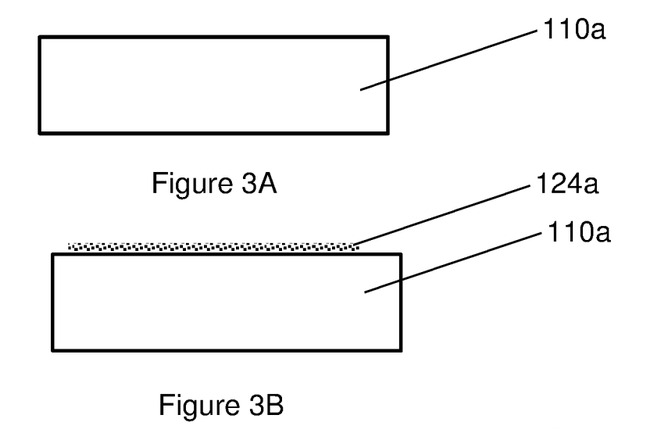
FIGS. 3A-3M show a method of manufacturing an implantable device.

An exemplary method of manufacturing the implantable device 100 is shown in FIGS. 3A-3M. Initially, a silicon wafer (i.e. "substrate") 110a is provided to form the body 110, as shown in FIG. 3A.

Figure 3C:
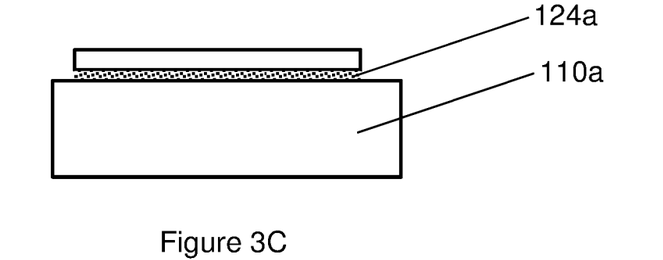
Figure 3D:
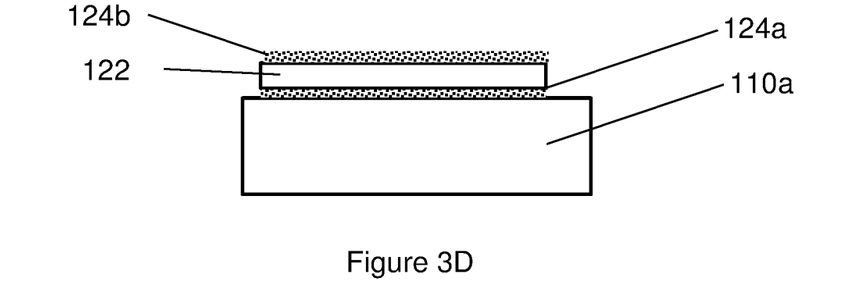

The BAW resonator 120 is then formed on top of the substrate 110a, as follows. A passivation layer of $SiO_2$ (or SiNi) is added to the upper surface of the substrate 110a before a first electrode 124a (for example, comprising molybdenum) is deposited as shown in FIG. 3B, for example by way of vapour deposition. A piezoelectric element 122, for example a (piezoelectric) aluminium nitride (AlN) 'thin' film, is then deposited onto the first electrode 124a, as shown in FIG. 3C. A second electrode 124b (for example, comprising aluminium) is then deposited onto the piezoelectric element 122, as shown in FIG. 3D to complete the BAW resonator 120. The BAW resonator 120 is formed with a space surrounding it on the upper surface of the body 110, to allow the acoustic reflector 130 to be formed, as will be described further on.

Figure 3E:
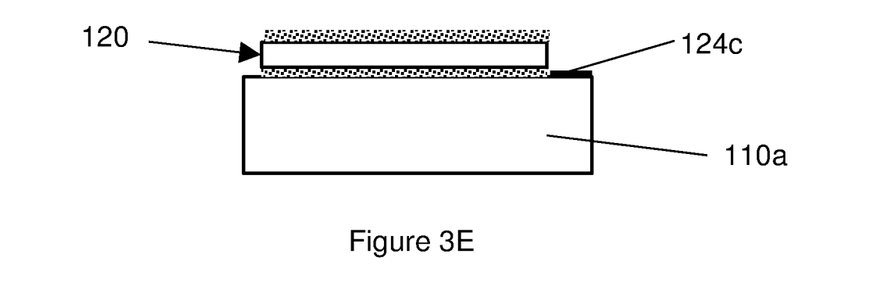

An electrical contact pad 124c is deposited onto the upper surface of the substrate 110a, as shown in FIG. 3E, the contact pad 124c being arranged to provide an electrical connection with the BAW resonator 120.

Figure 3F:
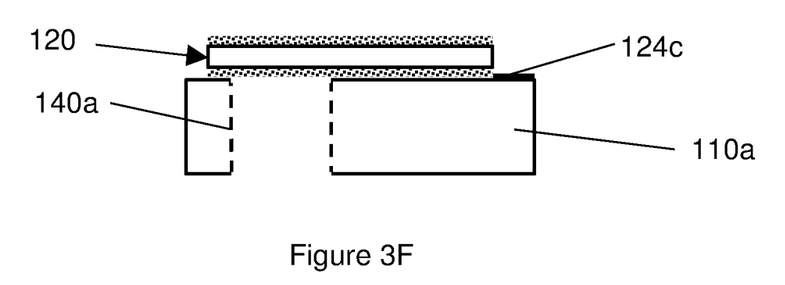
Figure 3G:
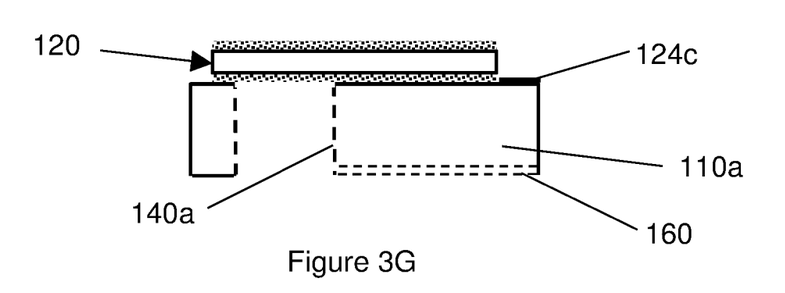
Figure 3H:
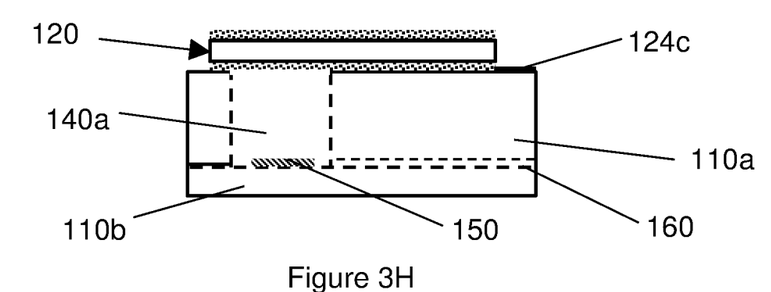

A hole 140a is then etched from the underside of the substrate 110a through to the upper surface of the substrate 110a, upon which is mounted the BAW resonator 120, as shown in FIG. 3F, for example by plasma or chemical etching, e.g. wet chemical etching. A groove 160 is also etched across the underside of the substrate 110a from an edge of the substrate 110a and into the hole 140a, as shown in FIG. 3G. A silicon cap 110b is then bonded to the underside of the substrate 110a to form the complete body 110, as shown in FIG. 3H. The cap may have mounted thereon sensing circuitry 150. In bonding the cap 110b to the substrate 110a, the hole 140a is closed to form the hermetically sealed 'reference' cavity 140a and the groove 160 is closed to form a via 160 provided an external connection to within the cavity 140a, as shown in FIG. 3I.

Figure 3I:
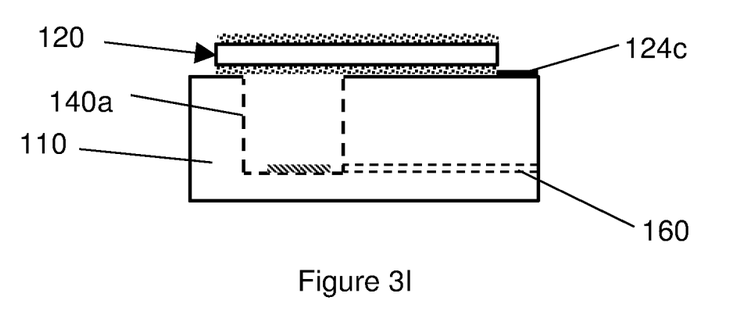

As can be seen from FIG. 3I, for example, while the BAW resonator 120 should be cantilevered over the cavity 140a, a small part of the cantilevered portion of the BAW resonator 120 may overlap onto the upper surface of the body 110 to facilitate convenient manufacture without affecting the ability of the BAW resonator 120 to function as required. The overlap may be around 10% of the width of the body 110, for example 20 microns for a body 110 having a width of 200 microns. Furthermore, as can also be seen from FIG. 3I, the depth of the cavity 140a into which the BAW resonator 120 may deflect (or deform) is a small fraction of the overall size (and depth) of the cavity 140a.

Figure 3J:
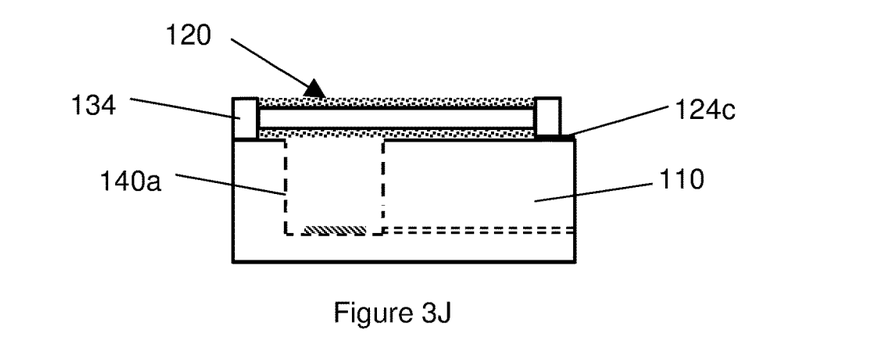
Figure 3K:
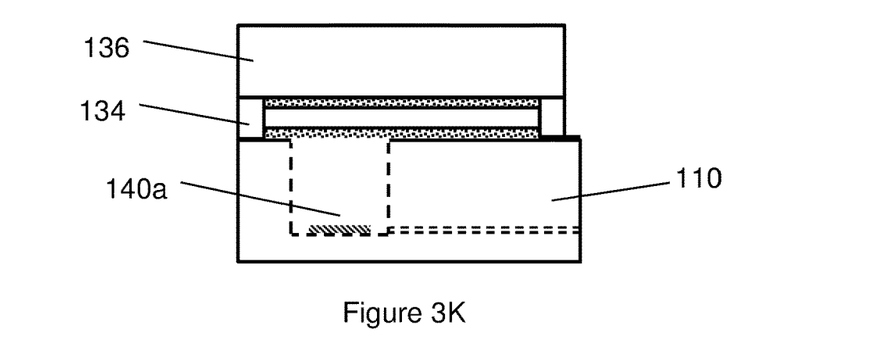
Figure 3L:
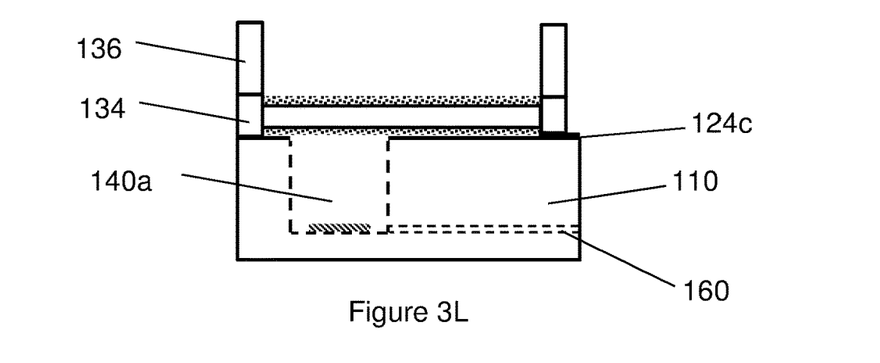
Figure 3M:
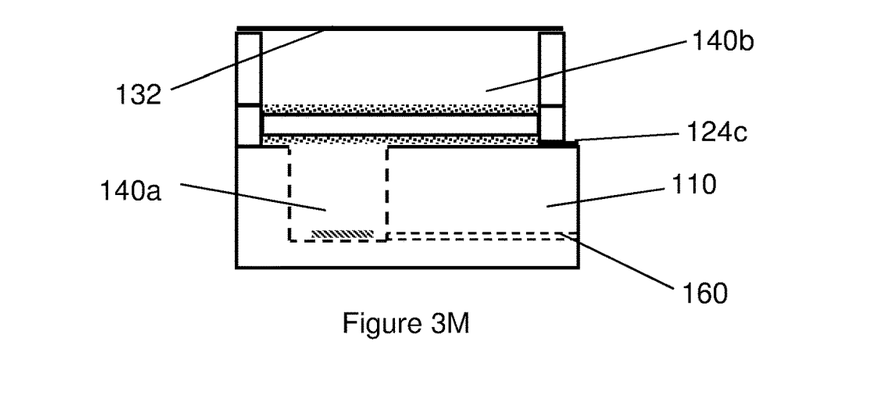

A silicon spacer 134 is bonded to the upper surface of the body, as shown in FIG. 3J. The spacer 134 is arranged to surround the BAW resonator 120, though the electrical contact pad 124c remains in electrical contact with the BAW resonator 120. A silicon wafer 136 is then bonded to the spacer 134, covering the BAW resonator 120, as shown in FIG. 3K. The wafer 136 is then etched so as to correspond with the shape of the spacer 134 and thereby expose the BAW resonator 120 beneath it, as shown in FIG. 3L. A metal layer 132, for example gold foil, is then bonded to the remaining silicon wafer 136, which acts as a support for the metal layer 132, as shown in FIG. 3M. The metal layer 132 may be (radially) corrugated to allow it to be easily displaced by external changes in intravascular pressure. The metal layer 132 and silicon support 136 thereby create a hermetically sealed chamber 140b containing a gas, such as air for example. The silicon wafer 136 may be substituted by a glass wafer containing sodium ions (not shown), which is suitable for bonding to silicon and which does not shatter.

The body 110 of the device 100 could of course be any size and shape that is suitable to be implanted into a human or animal body, which may be selected according to the species of animal, and/or the age, sex of the human or animal. For example, the device may have a length of around 200 microns. For example, the body 110 may be generally circular, oval or even tetrahedral if required, though a generally planar upper surface 110a (at least in part) onto which the BAW resonator 120 can be mounted may be advantageous.

The cavity 140a may alternatively have a circular cross-section, or indeed be of any other suitable shape that can accommodate sensor circuitry 150.

The via 160 may be arranged to accommodate one or more electrical wires (or similar electrical signal conduits) for communicating an electrical signal between the cavity 140 and the exterior of the body 110, or else the at least one via itself may be arranged to carry an electrical signal, for example it may be coated with an electrically conducting material (not shown). The at least one via 160 may comprise multiple vias arranged to communicate multiple electrical signals between the sensing circuitry 150 and the exterior of the device 100. The (or each) via 160 may be electrically isolated from each other (and the body 110) to keep electrical signals separate. One or more additional vias could pass through the body 110 from different sides 110c, 110d of the body 110 or even the top or bottom surfaces 110a, 110b, to provide additional conduits for electrical communication between sensing circuitry 150 provided on the body 110, for example in the cavity 140a. Sensing circuitry may of course be provided elsewhere on the body 110, optionally in addition to the sensor circuitry 150 disposed in the cavity 140a.

The tuning of an antenna coupled to the device may match the tuning of the BAW resonator such that the components linking them can be passive, for example.

In an aspect there is provided an implantable device for sensing intravascular pressure, the device comprising:
 a bulk acoustic wave (BAW) resonator arranged to be deflected by changes in intravascular fluid pressure to provide a pressure dependent sensing signal; and
 an acoustic isolator arranged to separate the BAW resonator from the intravascular fluid and to mediate pressure from the intravascular fluid to the BAW resonator; wherein the acoustic isolator comprises a gas filled chamber sealed by a (corrugated) metal membrane isolating the BAW resonator from the intravascular fluid.

Figure 4:
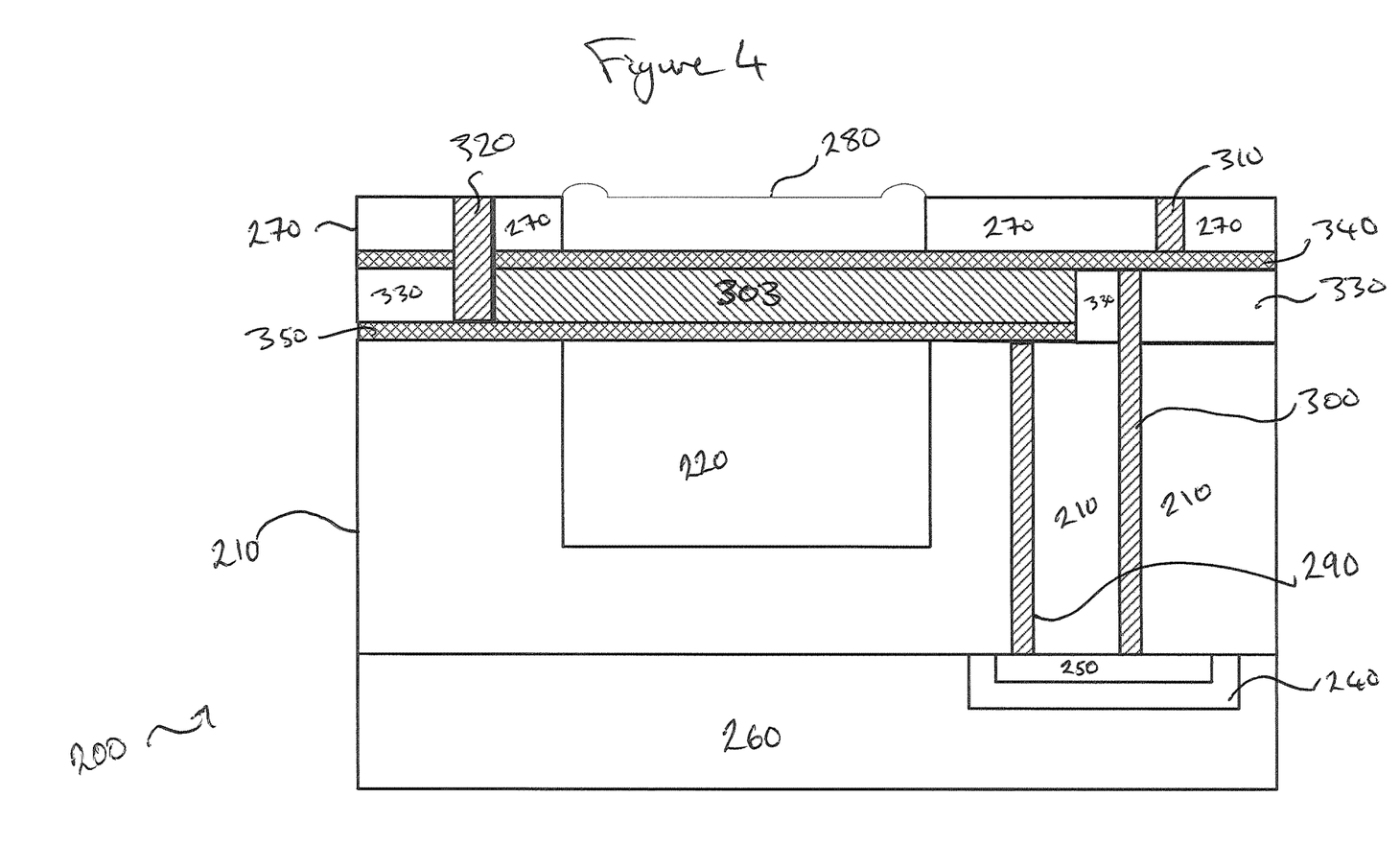
FIG. 4 shows a diagram of a section through an implantable device.

FIG. 4 shows an example of an implantable device 200 for sensing intravascular pressure. The device may be sized for implantation in a vascular lumen of an animal such as a human, typically an adult human. For example it may be of a size suitable for implantation in the pulmonary artery of a human, for example an adult human.

The device 200 shown in FIG. 4 comprises a body provided by a substrate 210 comprising a first cavity 220, and a first via, and a second via 300. The device 200 also comprises a BAW resonator 303, 340, 350 an insulator 330, a flexible layer such as a flexible membrane 280 (e.g. a metal foil, which may be corrugated). The device 200 also comprises a base 260, and a sensing circuit 250. The device 200 may also comprise a cap 270, to provide a rigid spacer between the substrate 210 and the flexible layer. The cap 270 may have a third via 310 and a fourth via to provide two separate electrical conduction paths through the cap 270.

In the example illustrated in FIG. 4, the substrate 210 is seated on the base 260, and the BAW resonator 303, 340, 350 and the insulator 330 are sandwiched between the cap 270 and the substrate 210. The cap 270 comprises an opening which overlies a region of the BAW resonator 303, and the opening in the cap 270 is covered by the flexible membrane 280 to provide a chamber between the BAW resonator 303 and the flexible membrane 280.

The chamber may be filled with a fluid, such as a gas, having a lower acoustic impedance than the BAW resonator 303 and optionally also a lower acoustic impedance than the intravascular fluid. The flexible membrane 280 may be corrugated and may be resilient. This chamber is sealed.

The first cavity 220 may be provided in a second side of the substrate 210 (e.g. opposite to the first side). The first cavity 220 may comprise a void in the second side of the substrate 210, which may have a cuboid shape. The cavity may be bounded by the substrate 210 on all but one of its sides. Its open side (e.g. on the second side of the substrate 210) may be covered by a BAW resonator 303 340, 350, which may be provided by a flat piece of piezo electric material.

The base 260 comprises a second cavity 240, and disposed in the second cavity 240 is the sensing circuit 250. The base 260 is secured to a first side of the substrate 210, so that the substrate 210 covers the second cavity 240 to enclose the sensing circuit 250. The first via 290 and the second via 300 may pass through the substrate 210 to provide an electrical conduction path to the second cavity 240.

The underside of the BAW resonator 303, 340, 350 may be secured to the substrate 210 on the second side of the substrate 210. For example it may cover the open side of the first cavity 220, and may be secured to the substrate 210 around the periphery of that cavity. Generally the first cavity 220 is completely enclosed, e.g. its open side is closed by the BAW resonator 303, for example the BAW resonator 303, 340, 350 may hermetically seal the first cavity 220. The BAW resonator 303, 340, 350 may however not completely cover the second side of the substrate 210. For example, an insulating material, such as a dielectric, may also be secured to the second side of the substrate 210 and at least partially surround the edges of the BAW resonator 303, 340, 350. For example the BAW resonator 303, 340, 350 may be bounded on at least two, and perhaps four, edges by the insulator 330, 340, 350. For example the BAW resonator 303, 340, 350 may be a flat structure secured on its underside (one major surface) to the second side of the substrate 210 whilst its minor surfaces (the edges of the flat structure) are bounded by the insulator 330 which may also be secured to parts of the second side of the substrate 210 which are not covered by the BAW resonator 303, 340, 350.

The piezoelectric material 303 of the BAW resonator 303, 340, 350 may have a first electrode 350 on its underside, and a second electrode 340 on its upper side.

The first via 290 may connect the sensing circuit 250 in the second cavity 240 to the first electrode 350. For example, the first via 290 may pass through the substrate 210 from the second cavity 240 to provide a conduction path from the circuit in the second cavity 240 to the first electrode 350.

The second via 300 may pass through the substrate 210 from the second cavity 240 to provide a conduction path from the circuit in the second cavity 240 to the second electrode 340. For example, a conductive material may extend across at least a part of the upper surface of the insulator 330 to provide a connection to the second electrode 340. For example the second electrode 340 may comprise a conductive layer which extends across the upper surface of the BAW resonator 303 and outward from it to cover at least a first part of the upper surface of the insulator 330. Accordingly, to make electrical contact between the sensing circuit 250 and the second electrode 340, the second via 300 may pass from a region on the first side of the substrate 210 which covers the second cavity 240, through the substrate 210 and then through this first part of the insulator 330.

The third via 310 may pass from the upper surface of the cap 270, through the cap 270 to connect with the second electrode 340, for example on the first part of the insulator 330 which is covered by conductive material connected to the second electrode 340.

The fourth via 320 may pass from the upper surface of the cap 270, and through the insulator 330, to make electrical contact with the first electrode 350. For example the first electrode 350 may comprise a conductive material which extends across the underside of the BAW resonator 303 and out from it so that it underlies a second part of the insulator 330. In some embodiments the fourth via 320 may also pass through a region of the first part of the insulator 330 to make this connection. In other words in some regions the lower and upper surface of the insulator 330 may carry conductive material electrically connected to the first and second electrodes 350, 340 respectively.

The third via 310 and fourth via 320 may enable an excitatory signal to be connected to the BAW resonator 303, e.g. from an antenna which may be connected to provide an alternating voltage between the third via 310 and the fourth via 320.

The vias 290, 300 may comprise conductive material, for example they may be lined or filled with conductive material such as copper.

In use, the device 200 illustrated in FIG. 4 can be connected, by the third and fourth vias 310, 320 to an antenna. The device 200 and the antenna may be implanted into a vascular lumen (such as a vein or artery). The antenna may be tuned for sending and receiving RF signals having a frequency band corresponding to a resonant frequency of the BAW resonator 303.

In response to variations in intravascular pressure (e.g. blood pressure) the flexible membrane 280 may be deflected thereby causing a corresponding variation in pressure in the chamber of fluid held between the membrane 280 and the BAW resonator 303. This change in pressure in turn causes deflection of the BAW resonator 303 according to the pressure difference between the fluid in the chamber and the pressure in the first cavity 220 (in the substrate 210 beneath the BAW resonator 303). The resonant characteristics of the BAW resonator 303 may vary in dependence upon these deflections, and the sensing circuitry may be coupled to the BAW resonator 303 for sensing changes in this characteristic. Optionally, the sensing circuit may provide a response signal through the first and second vias, to be provided to the antenna (not shown) through the third and fourth vias respectively. The antenna can thus provide pressure dependent signals to an RF device outside the body of the subject in whom the device is implanted.

Thus it can be seen that the membrane 280 and chamber of fluid act to mediate changes in pressure in the intravascular fluid to the BAW resonator 303. In addition, this same structure—the membrane 280, and the sealed chamber of fluid it holds against the BAW resonator 303 act to provide transitions in acoustic impedance between the BAW resonator 303 and the surrounding intravascular fluid. These layers of differing acoustic impedance, and the transitions in acoustic impedance between layers may provide reflections of acoustic energy to reduce the transmission of acoustic energy from the BAW resonator 303 into the intravascular fluid. For example the transition in acoustic impedance (from BAW resonator 303, to fluid in chamber) may cause acoustic energy to stay within the BAW resonator 303, e.g. to be reflected at the boundary between the BAW resonator 303 and the fluid (gas) in the chamber. This provides a form of acoustic reflector, which reduces the loading which the intravascular fluid may otherwise place on the BAW resonator 303. For example, it may isolate the BAW resonator 303 from that acoustic load.

To the extent that certain methods may be applied to the living human or animal body, it will be appreciated that such methods may not provide any surgical or therapeutic effect. In addition, it will be appreciated that such methods may be applied ex vivo, to tissue samples that are not part of the living human or animal body. For example, the methods described herein may be practiced on meat, tissue samples, cadavers, and other non-living objects. For example, embodiments of the disclosure provide methods of sensing intravascular pressure comprising deploying a device such as any one of those described herein into a vascular lumen of a subject, and interrogating the device by transmitting RF signals tuned to excite the BAW resonator 303 into the body of the subject.

As used herein, the articles "a" and "an" may refer to one or to more than one (e.g., to at least one) of the grammatical object of the article.

"About" may generally mean an acceptable degree of error for the quantity measured given the nature or precision of the measurements. Exemplary degrees of error are within 20 percent (%), typically, within 10%, and more typically, within 5% of a given value or range of values.

With reference to the drawings in general, it will be appreciated that schematic functional block diagrams are used to indicate functionality of systems and apparatus described herein. It will be appreciated however that the functionality need not be divided in this way, and should not be taken to imply any particular structure of hardware other than that described and claimed below. The function of one or more of the elements shown in the drawings may be further subdivided, and/or distributed throughout apparatus of the disclosure. In some embodiments the function of one or more elements shown in the drawings may be integrated into a single functional unit.

The above embodiments are to be understood as illustrative examples. Further embodiments and aspects of an implantable device are envisaged. It should be understood that any feature described in relation to any one embodiment may be used alone, or in combination with other features described, and may also be used in combination with one or more features of any other of the embodiments, or any combination of any other of the embodiments. Any apparatus feature as described herein may also be provided as a method feature, and vice versa. Furthermore, equivalents and modifications not described above may also be employed without departing from the scope of the invention, which is defined in the accompanying claims

The invention claimed is:

1. An implantable device for sensing intravascular pressure, the device comprising:
   a bulk acoustic wave (BAW) resonator arranged to be deflected by changes in intravascular fluid pressure to provide a pressure dependent sensing signal; and
   an acoustic reflector arranged to separate the BAW resonator from the intravascular fluid and to mediate pressure from the intravascular fluid to the BAW resonator; wherein the acoustic reflector comprises a layer structure arranged to provide a series of transitions in acoustic impedance between the intravascular fluid and the BAW resonator, wherein the layer structure comprises a flexible layer which encloses a fluid layer between the flexible layer and the BAW resonator.

2. The device of claim 1, wherein the fluid layer has a lower acoustic impedance than the intravascular fluid.

3. The device of claim 2, wherein the fluid layer comprises a gas layer.

4. The device of claim 1, wherein the fluid layer is held in a sealed enclosure provided at least in part by the flexible layer.

5. The device of claim 1, further comprising a rigid spacer which surrounds the fluid layer and supports the flexible layer spaced from the BAW resonator.

6. The device of claim 1, further comprising a body carrying the BAW resonator, wherein the BAW resonator is disposed between the acoustic reflector and the body.

7. The device of claim 6, wherein the body comprises a cavity of fluid at a reference pressure arranged so that the BAW resonator can be deflected into the cavity in response to changes in intravascular pressure.

8. The device of claim 7, wherein the body is joined to the BAW resonator by a hermetic bond which closes the cavity.

9. The device of claim 7, comprising sensor circuitry disposed in the body and arranged to provide an alternating electrical signal to the BAW resonator.

10. The device of claim 9, wherein the sensor circuitry is disposed in the cavity.

11. The device of claim 6, wherein the body comprises silicon.

12. The device of claim 1, wherein said at least one layer has a thickness of around 1 micron.

13. The device of claim 1, wherein the flexible layer comprises a metal foil, for example a gold foil.

14. The device of claim 1, wherein the BAW resonator comprises aluminium nitride (AlN).

15. The device of claim 1, wherein the series of transitions in acoustic impedance comprise at least three transitions.

16. The device of claim 9 wherein the device comprises a second cavity, separate from the cavity of fluid at reference pressure.

17. An implantable device for sensing intravascular pressure, the device comprising:
   a bulk acoustic wave (BAW) resonator arranged to be deflected by changes in intravascular fluid pressure to provide a pressure dependent sensing signal; and
   an acoustic reflector arranged to separate the BAW resonator from the intravascular fluid and to mediate pressure from the intravascular fluid to the BAW resonator, the acoustic reflector comprising a layer structure arranged to provide a series of transitions in acoustic impedance between the intravascular fluid and the BAW resonator, the layer structure comprising a metal foil flexible layer which encloses a fluid layer between the metal foil flexible layer and the BAW resonator;
   a body carrying the BAW resonator, wherein the BAW resonator is disposed between the acoustic reflector and the body, the body comprising a cavity of fluid at a reference pressure arranged so that the BAW resonator can be deflected into the cavity in response to changes in intravascular pressure, wherein the body is joined to the BAW resonator by a hermetic bond which closes the cavity;
   sensor circuitry disposed in the cavity of the body and arranged to provide an alternating electrical signal to the BAW resonator; and
   at least one via in the body.

* * * * *